United States Patent
Preuthun et al.

(10) Patent No.: US 6,786,890 B2
(45) Date of Patent: Sep. 7, 2004

(54) LINEAR ACTUATOR AND A MEDICAL DELIVERY DEVICE COMPRISING SUCH LINEAR ACTUATOR

(75) Inventors: Jan Harald Preuthun, Bronshoj (DK); Soren Henrik Ljunggreen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/349,009

(22) Filed: Jan. 22, 2003

(65) Prior Publication Data

US 2004/0000818 A1 Jan. 1, 2004

Related U.S. Application Data

(60) Provisional application No. 60/355,893, filed on Feb. 11, 2002.

(30) Foreign Application Priority Data

Jan. 25, 2002  (DK) ........................................ 2002 00131

(51) Int. Cl.[7] ............................................ A61M 37/00
(52) U.S. Cl. ..................................................... 604/155
(58) Field of Search ........................ 604/30–34, 65–67, 604/131, 154, 155, 156, 315; 128/DIG. 1, DIG. 12, DIG. 13

(56) References Cited

U.S. PATENT DOCUMENTS 5,282,593 A    2/1994  Fast ........................ 248/188.4
6,067,868 A    5/2000  Nakamura et al. ......... 74/89.15

FOREIGN PATENT DOCUMENTS

| DE | 2301 964 | 8/1973 |
|---|---|---|
| DE | 3910814 A1 | 10/1993 |
| WO | 96/18826 | 6/1996 |
| WO | 98/47552 | 10/1998 |
| WO | 01/78556 A1 | 10/2001 |

*Primary Examiner*—Manuel Mendez
(74) *Attorney, Agent, or Firm*—Reza Green, Esq.; Richard W. Book, Esq.; Marc A. Began, Esq.

(57) ABSTRACT

A linear actuator comprising a first member (1) and a second member (2) provided with internal threads (6,8) cut in opposite directions and an intermediary member (3) engaged with and being axially displaceable in relation to the first and second members (1,2), via external threads (11,12) that are complementary to the threads (6,8) provided on the first and second members (1,2). The linear actuator furthermore comprises a sheath (4) stretching across the intermediary member (3), which sheath (4) is inrotatably, but longitudinally slidably arranged in relation to the first and second members (1,2). The linear actuator also comprises a driving rod (5) that is inrotatably, but longitudinally slidably arranged within the intermediary member (3). A medical delivery device provided with such a linear actuator is also provided.

13 Claims, 2 Drawing Sheets

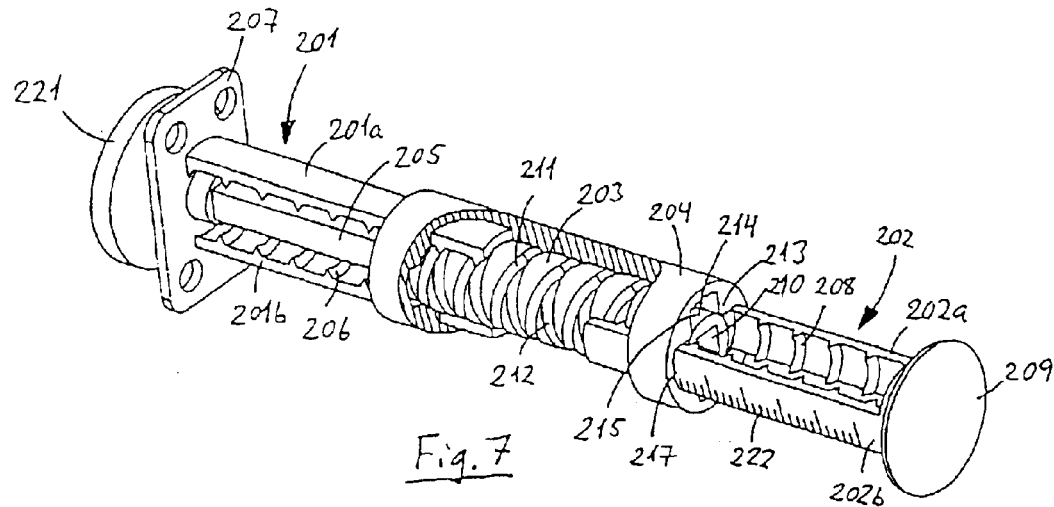
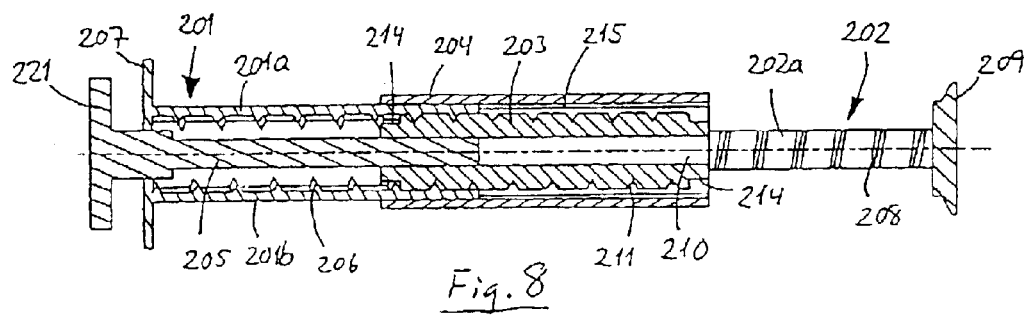
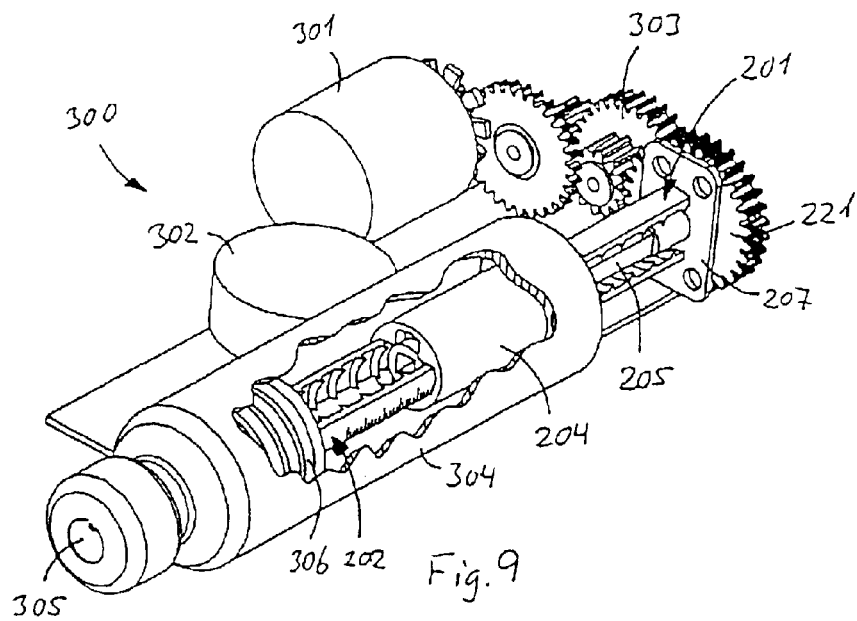

LINEAR ACTUATOR AND A MEDICAL DELIVERY DEVICE COMPRISING SUCH LINEAR ACTUATOR

CROSS-REFERENCE TO RELATED APPLICATIONS

This application claims priority under 35 U.S.C. 119 of U.S. provisional application No. 60/355,893 filed Feb. 11, 2002 and Danish application no. PA 2002 00131 filed Jan. 25, 2002; the contents of both are fully incorporated herein by reference.

BACKGROUND OF THE INVENTION

The invention relates to a linear actuator comprising a first member provided with threads cut in a first direction;

a second member provided to be axially displaceable in relation to the first member and being provided with threads cut in a second direction opposite said first direction;

an intermediary member being engaged with and axially displaceable in relation to the first and second members, respectively, via first and second threads that are complementary to the threads provided on the first and second members, respectively;

means for preventing rotation of the first member in relation to the second member; and drive means for rotationally driving the intermediary member.

The invention also relates to a medical delivery device comprising such a linear actuator provided as a piston rod.

A linear actuator of this type in the form of a telescopic piston rod is known from the medical delivery device shown in WO 98/47552 that discloses a propelling device for a piston in a container containing a liquid medicament. In one embodiment of the device, the first member constitutes a housing and the second member and the intermediary member extend telescopically from the housing. The intermediary member has the form of a tube provided with an external thread cut in a first direction over its entire length. The thread is complementary to a thread cut in the housing. A gear wheel is rotatably connected to the housing and is inrotatably but longitudinally slidably connected to the intermediary member. This means that when the gear wheel is rotated in relation to the housing, the intermediary member is forced to rotate which, in turn, displaces it out of or into the housing due to the complementary threads cut in the housing and on the outer surface of the intermediary member. The second member is positioned within the intermediary member and it also has the shape of a tube with an external thread over its entire length. This external thread is complementary to an internal thread at the distal end of the intermediary member. These threads are cut in the opposite direction of the external thread of the intermediary member. A guiding rod is provided inrotatably but slidably within the housing and it extends through the intermediary member and is inrotatably but slidably engaged with the interior of the second member. Thus, the guiding rod prevents the housing and the second member from mutual rotation.

Telescopic displacement of the linear actuator is achieved by rotation of the gear wheel which, in turn, forces the intermediary member to rotate and thereby to be displaced out of the housing due to the interaction between its external thread and the thread provided in the housing. The rotation of the intermediary member furthermore displaces the second member out of the intermediary member since the second member is inrotatably arranged in relation to the housing and since the external thread of the second member is opposite the external thread provided on the intermediary member. In this way rotation of the gear wheel causes a telescopic displacement of the intermediary member, the rotation of which, in turn, causes a further telescopic displacement of the second member.

In the linear actuator provided as a telescopic piston rod described above, the exterior surfaces of the intermediary member as well as the second member are provided with threads. In applications where it would be desirable to provide the exterior surfaces of the piston rod with a kind of information, such as a colouring pattern, a scale, a name, etc., this is hardly accomplishable due to the uneven and threaded surfaces. If information is applied to the threaded surfaces it will most likely be worn off over time due to the friction between the members of the linear actuator.

It is therefore an object of the invention to provide a linear actuator of the type mentioned in the opening paragraph that is provided with smooth exterior surfaces that are suitable for incorporation and display of different kinds of information.

SUMMARY OF THE INVENTION

This object is achieved by arranging the linear actuator mentioned in the opening paragraph such that the threads provided on the first and second members are provided as internal threads;

that the threads provided on the intermediary member are provided as external threads;

that the means for preventing rotation of the first member in relation to the second member comprises an outer sheath stretching across the intermediary member, said sheath being inrotatably but longitudinally slidably arranged in relation to the first and second members; and that the drive means comprises a driving rod that is inrotatably but longitudinally slidably arranged within the intermediary member.

Thereby is obtained that no threads are positioned on the exterior surfaces of neither the first member nor the second member nor on the sheath stretching across the intermediary member. Each of these surfaces may therefore have any desired form and smoothness that allow any kind of information to be displayed thereon. The smooth surfaces also calls for easier cleaning than the threaded surfaces of the prior art linear actuators of the type in question.

Preferably, the sheath is cylinder-shaped with a closed cylinder face with ample opportunities for displaying information thereon.

In first and second embodiments for a linear actuator according to the invention the first and second members are tube-shaped with smooth exterior surfaces that also give ample opportunities for displaying information thereon.

Preferably, the first member has an inner diameter that exceeds an outer diameter of the sheath, and preferably the sheath has an inner diameter that exceeds an outer diameter of the second member, while the intermediary member generally has a smaller diameter than an inner diameter of the second member, except for a part at one end that is provided with the external threads that engage the internal threads of the first member. This structure of the linear actuator gives a true telescopic appearance of the linear actuator, exposing only smooth surfaces. The smooth surfaces makes it possible to seal the exposed parts in relation to each other, e.g. by means of O-rings.

In the first embodiment of the invention ordinary threads are employed, but in the second embodiment of the invention the external threads provided on the intermediary member are formed by a plurality of balls that protrude from a ball track in a re-circulating ball arrangement. By this arrangement the friction between the intermediary member and the first and second members is reduced considerably, which increases the efficiency of the threaded connection.

In order to prevent the first and second members from rotating relative to each other the sheath is preferably provided with at least one external tongue that engages an internal longitudinal groove provided in the first member, while the second member is provided with at least one external tongue that engages an internal longitudinal groove provided in the sheath.

In a third embodiment of a linear actuator according to the invention the intermediary member is provided with crossing threads, while each of the first member and the second member has at least one leg, which legs complement each other circumferentially around the intermediary member. In this embodiment the overall diameter of the linear actuator can be less than the overall diameter in the first and second embodiments, since the diameter of the threaded parts can be maintained at a level corresponding to the smallest diameter in the first and second embodiments. A reduction of the diameter entails an increase of the angle of pitch, which in turn increases the efficiency of the threaded connection.

Each of the first and second members preferably has two legs, each with a circumferential expanse of less than 90°. Providing only two legs at each member simplifies the structure thereof and gives opportunities to provide relatively large surfaces for displaying information.

In this embodiment the sheath has an inner diameter that exceeds the outer diameters of the first and second members, while it is provided with internal grooves that engage the legs of the first and second members. In this embodiment the sheath with ample opportunities for being provided with information is fully visible at all times since it covers the first as well as the second member.

When the linear actuator according to the invention is employed as a piston rod in a medical delivery device provided with a cartridge with a liquid medicament, it is preferably arranged in such a way that neither the second member nor the sheath has an outer dimension that exceeds an inner diameter of the cartridge. Thereby the second member as well as the sheath of the linear actuator can be expanded into the cartridge for expelling the liquid medicament therefrom.

In a preferred embodiment of the medical delivery device the driving rod is provided with a gear wheel that is connected to a driving mechanism, such as an electric motor.

BRIEF DESCRIPTION OF THE DRAWING

The invention will be discussed in further detail below with reference to the drawing in which FIG. 1 shows a partially sectional view of a first embodiment of a linear actuator according to the invention;

FIG. 2 shows a cross-section of the first embodiment of a linear actuator according to the invention;

FIG. 3 shows a cross-section of a second embodiment of a linear actuator according to the invention;

FIG. 4 shows an end view of the intermediary member of the second embodiment of a linear actuator according to the invention;

FIG. 5 shows a side view of the intermediary member of the second embodiment of a linear actuator according to the invention;

FIG. 6 shows a perspective view of the second embodiment of a linear actuator according to the invention;

FIG. 7 shows a partially sectional view of a third embodiment of a linear actuator according to the invention;

FIG. 8 shows a cross-section of the third embodiment of a linear actuator according to the invention; and FIG. 9 shows a partially sectional view of a medical delivery device provided with a linear actuator as a piston rod according to the third embodiment.

DETAILED DESCRIPTION OF THE INVENTION

Figures 1, 2, 3, 4, 5, 6:
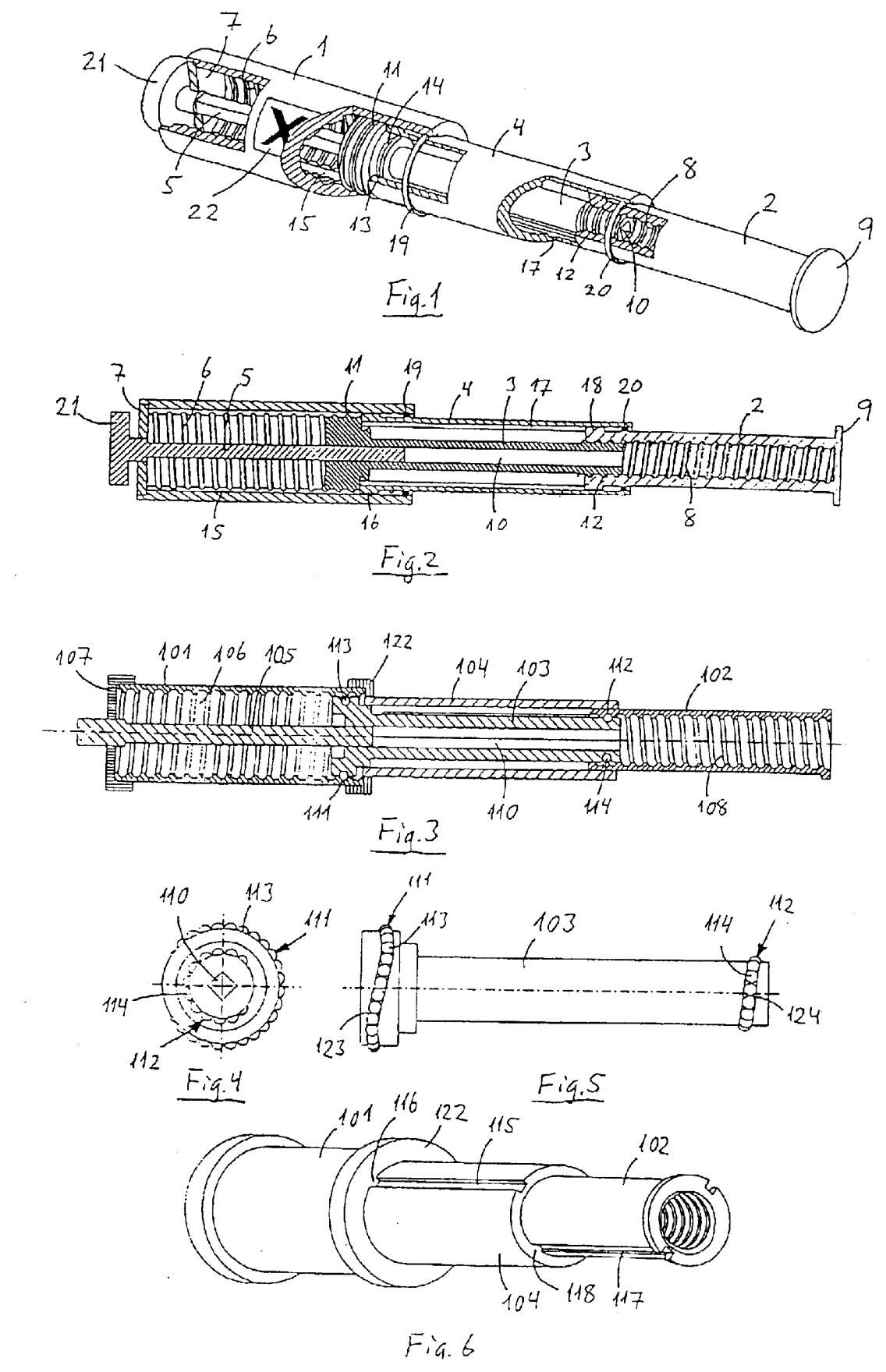

A first embodiment of a linear actuator according to the invention is shown in FIGS. 1 and 2. The linear actuator comprises a first member 1, a second member 2, an intermediary member 3, a sheath 4 and a driving rod 5, and these members are assembled as shown. In FIG. 1 the first member 1, the second member 2 and the sheath 4 is shown with some parts cut away for better illustration, and in FIG. 2 all parts are shown in an axial cross-section through the linear actuator.

The first member 1 is shaped as a tubular cylinder with a smooth outer surface and is provided with an internal thread 6 cut in a first direction. A lid 7 is provided at one end of the first member 1 and is secured thereto by any suitable means.

The second member 2 is generally also shaped as a tubular cylinder with a smooth outer surface and is provided with an internal thread 8 cut in a second direction opposite the first direction of the thread 6 in the first member 1. A pressure plate 9 is provided at one closed end of the second member 2. The second member 2 has in this embodiment a smaller diameter than the first member 1.

The intermediary member 3 is also tubular with a centrally located through-going opening 10. At each end the intermediary member 3 is provided with external threads 11,12 that are complementary with the internal threads 6,8 provided in the first and second members, respectively; i.e. the threads 11,12 are cut in opposite directions. The intermediary member 3 has over most of its length a diameter that is smaller than the inner diameter of the second member 2, so that the second member 2 can be telescopically displaced in relation to the intermediary member 3 by means of the internal thread 8 of the second member 2 and the complementary external thread 12 of the intermediary member. One end of the intermediary member 3 has a threaded part of a larger diameter, which essentially corresponds to the inner diameter of the first member 1, thereby allowing the intermediary member 3 to be telescopically displaced in relation to the first member 1 by means of the internal thread 6 of the first member 1 and the complementary external thread 11 of the intermediary member 3.

The sheath 4 is generally cylinder-shaped with a closed and smooth cylinder face. The sheath 4 has an outer diameter that essentially equals the inner diameter of the first member 1 and an inner diameter that essentially equals the outer diameter of the second member 2. Thereby the sheath 4 is allowed to be telescopically displaced in relation to the first and second members 1,2, respectively. The sheath 4 follows the displacement of the intermediary member 3 by means of a bead 13 that is engaged with an undercut groove 14 provided in the intermediary member 3.

The purpose of the sheath 4 is to expose a smooth surface surrounding the intermediary member 3 and to prevent the first and second members 1,2 from being mutually rotated when the intermediary member 3 is rotated as it will be described below. In order to achieve this last-mentioned function, at least one and preferably two longitudinal grooves 15 are provided in the inner surface of the first member 1 while the sheath 4 is provided with tongues 16 that engage the grooves 15, and similarly the inner surface of the sheath 4 is provided with at least one and preferably two longitudinal grooves 17 while the second member 2 is provided with tongues 18 that engage the grooves 17. In this way the sheath 4 is prevented from being rotated in relation to both the first and the second member 1,2 while it still may be longitudinally displaced in relation thereto.

O-rings 19,20 are provided in order to seal the movable parts of the linear actuator in relation to each other, and the smooth outer surfaces of the parts facilitate the sealing.

As mentioned above, the intermediary member 3 is provided with a central through-going opening 10 which, in the shown embodiment, has a square cross-section as shown in FIG. 1. The driving rod 5, which extends into the through-going opening 10 in the intermediary member 3, has a similar cross-section that makes it inrotatably, but slidably engaged with the intermediary member 3. At the outer end of the driving rod 5 a gear wheel 21 is provided. When the linear actuator is mounted in a device, such as a medical delivery device to serve as a telescopic piston rod, as it will be described below with reference to FIG. 9, the gear wheel 21 will be connected to an electric motor that rotates the gear wheel 21 and thereby the driving rod 5. The driving rod 5 has an extension that essentially corresponds to the length of the first member 1 and is retained axially in relation thereto in a not shown manner.

In operation the linear actuator is often initially in its retracted or its expanded state. In the following it is assumed that the linear actuator initially is in its retracted state where the intermediary member 3, the sheath 4 and the second member 2 are located within the first member 1 with the pressure plate 9 being just outside the first member 1. This situation is not shown, but can easily be imagined when viewing FIGS. 1 and 2.

When it is desired to extend the linear actuator, the driving rod 5 is rotated by means of the gear wheel 21. This causes the intermediary member 3 to be rotated and thereby to be displaced telescopically out of the first member 1 due to the engagement between the internal threads 6 in the first member 1 and the external threads 11 on the intermediary member 3.

The sheath 4 is also displaced axially out of the first member 1 and due to the engagement between the grooves 15 provided on the inner surface of the first member 1 and the tongues 16 provided on the outer surface of the sheath 4 it does not rotate. Since a similar engagement exists between the sheath 4 and the second member 2, i.e. the grooves 17 provided in the inner surface of the sheath 4 and the tongues 18 provided at the outer surface of the second member 2, the second member 2 is also prevented from rotating. Therefore, rotation of the intermediary member 3 causes an axial displacement of the second member 2 in relation thereto due to the internal threads 8 provided in the second member and the external threads 12 provided on the intermediary member 3. Since the threads 8,12 are cut in the opposite direction of the threads 6,11, rotation of the intermediary member 3 causes the second member 2 to be displaced out of the sheath 4. The total expansion of the linear actuator is therefore defined as the sum of the displacement of the intermediary member 3 in relation to the first member 1 and the displacement of the second member 2 in relation to the intermediary member 3.

When it is desired to bring the linear actuator back to its initially retracted position, the gear wheel 21 is rotated in the opposite direction which causes the intermediary member 3 and the sheath 4 to be displaced into the first member 1 and the second member 2 to be displaced into the sheath 4.

Due to the structure of the linear actuator, which exposes smooth surfaces only, it is specifically suitable for displaying information. One example of such information is applied to the first member 1 in form of a sign 22 which may indicate the manufacturer of the linear actuator or of the device in which it is employed. If the device is a medical delivery device, the sign 22 may also indicate the type of cartridge or medicament that must be used in connection with the medical delivery device. Other kinds of information may also be displayed.

A cross-section of a second embodiment of a linear actuator according to the invention is shown in FIG. 3. This linear actuator corresponds essentially to the linear actuator shown in FIGS. 1 and 2 with the major differences being that the threaded connections comprise re-circulating ball arrangements.

The linear actuator according to the second embodiment comprises a first member 101, a second member 102, an intermediary member 103, a sheath 104 and a driving rod 105, and these members are assembled as shown. The first member 101 is shaped as a tubular cylinder with a smooth outer surface and is provided with an internal semicircular-shaped thread 106 cut in a first direction. A lid 107 is provided at one end of the first member 101 and is secured thereto by any suitable means. At the other end of the first member 101, an anti-rotation ring 122, which will be described in details below, is provided.

The second member 102 is also shaped as a generally tubular cylinder with a smooth outer surface and is provided with an internal semicircular-shaped thread 108 cut in a second direction opposite the first direction of the thread 106 in the first member 101. The shape of the thread 108 may, of course, have any other form suitable for supporting balls or other rolling bodies.

The intermediary member 103 is also generally tubular with a centrally located through-going opening 110. At each end the intermediary member 103 is provided with external threads 111,112 formed by a plurality of balls 113,114 protruding from two semicircular-shaped ball tracks 123, 124. The ball tracks 123,124 have over most of their expanse a depth that corresponds to the radius of the balls 113,114, and the ball tracks 123,124 are in these areas complementary with the internal threads 106,108 provided in the first and second members, respectively, i.e. the pitch of the ball tracks 123,124, and thereby of the external threads 111,112, corresponds to the pitch of the internal threads 106,108, respectively.

As shown in FIGS. 4 and 5, each ball track 123;124 extends circumferentially around the intermediary member 103, and the expanse in which the ball track 123;124 is complementary with the internal thread 106;108 is approximately 270°. In the remaining approximately 90° of the expanse of the ball track 123;124, the ball track 123;124 forms a re-circulating path for the balls 113;114 in which the depth of the ball track 123;124 is gradually increased to a depth corresponding to the diameter of the balls 113;114. Thereby, the re-circulating path allows the balls 113;114 to return to the part of the ball track 123;124 that is complementary with the thread 106;108.

In the embodiment shown in FIG. 4 the re-circulating paths of the ball tracks 123,124 are located diametrically opposite each other, which, however, is not important for the operation of the re-circulating ball arrangements.

As it was the case in the first embodiment described above, the sheath 104 is cylinder-shaped with a closed and generally smooth cylinder face. The sheath 104 generally also has the same function as described above and it will not be described in more detail.

The anti-rotation arrangements between the first member 101 and the sheath 104 and between the sheath 104 and the second member 102 are shown in FIG. 6. It is seen that the anti-rotation ring 122 connected to the first member 101 is provided with a tongue 116 (or preferably two tongues 116 positioned diametrically opposite each other) that engages a longitudinal groove 115 (or grooves 115) provided in the outer surface of the sheath 104. Similarly, the sheath 104 is provided with a tongue 118 (or preferably two tongues 118 positioned diametrically opposite each other) that engages a longitudinal groove 117 (or grooves 117) provided in the outer surface of the second member 102.

The linear actuator according to the second embodiment of the invention operates in exactly the same manner as the linear actuator according to the first embodiment of the invention, i.e. rotating of the driving rod 105 causes the intermediary member 103 to rotate, whereby the first and second members 101,102 are caused to be telescopically displaced in relation to the intermediary member 103. Due to the re-circulating ball arrangements the friction between the intermediary member 103 and the first and second members 101,102, respectively, is reduced considerably. This means that less torque is required for rotating the driving rod 105 in this second embodiment than was the case in the first embodiment. This further entails that the motor for driving the driving rod 105 can be smaller and that a slighter gearing between the motor and the driving rod 105 can be applied.

A third embodiment of a linear actuator according to the invention is shown in FIGS. 7 and 8. The linear actuator comprises a first member 201, a second member 202, an intermediary member 203, a sheath 204 and a driving rod 205, and these members are assembled as shown. In FIG. 7 the sheath 204 is shown with some parts cut away for better illustration, and in FIG. 8 all parts are shown in an axial cross-section through the linear actuator.

In this embodiment the first member 201 is U-shaped with two legs 201a,201b protruding from an end plate 207 that is arranged for mounting the first member 201 in a suitable device, such as a medical delivery device. The two legs 201a,201b have smooth outer surfaces and are provided with an internal thread 206 cut in a first direction.

The second member 202 is also U-shaped with two legs 202a,202b protruding from a pressure plate 209 that is arranged for abutting on e.g. a piston or a stopper provided in a cartridge when the linear actuator is mounted in a medical delivery device. The legs 202a,202b also have smooth outer surfaces and are provided with an internal thread 208 cut in a second direction opposite the first direction of the thread 206 in the first member 201. It will be noted that in this embodiment the general inner and outer diameters of the first and second members 201,202 are equal.

Also in this embodiment the intermediary member 203 is tubular with a centrally located through-going opening 210. The intermediary member 203 has the same outer diameter over almost its entire length, and the surface is provided with an external thread 211 cut in a first direction and being complementary with the internal thread 206 in the first member 201 and with an external thread 212 cut in a second direction and being complementary with the internal thread 208 in the second member 202. Since the two threads 206,208 are cut in opposite directions the threads 206,208 form a crossing pattern on the surface of the intermediary member 203 as shown in FIG. 7.

Since the intermediary member 203 has an outer diameter that equals the inner diameter of the first and second members 201,202 and the external threads 211,212 provided on the intermediary member 203 are in engagement with the internal threads 206,208 provided on the first and second members 201,202, the first and second members 201,202 can be telescopically displaced in opposite directions in relation to the intermediary member 203 by rotating the intermediary member 203. At each end the intermediary member has a cylindrical part 214 with smaller diameter than the general diameter of the intermediary member 203; these parts 214 being provided for receiving a part of the sheath 204 as explained below.

The sheath 204 is generally cylinder-shaped with a closed and smooth cylinder face even though a part has been cut away in FIG. 7 for better illustration. The sheath 204 has an outer diameter that spans over the legs 201a,201b,202a,202b of the first and second members 201,202, such that the legs 201a,201b,202a,202b of the first and second members 201,202 are covered by the sheath 204. The sheath 204 is provided with a pair of first internal longitudinal grooves 215 that inrotatably, but slidably, receive the legs 201a,201b of the first member 201 and with a pair of second internal longitudinal grooves 217 that inrotatably, but slidably, receive the legs 202a,202b of the second member 202.

At each end the sheath 204 is further provided with inwardly oriented protrusions 213 that define a central opening complementary to the cylindrical parts 214 of the intermediary member 203. The co-operation between these protrusions 213 and the cylindrical parts 214 prevents the sheath from being displaced axially in relation to the intermediary part 203.

The purpose of the sheath 204 is again to expose a smooth surface surrounding the intermediary member 203 and to prevent the first and second members 201,202 from being mutually rotated when the intermediary member 203 is rotated as it will be described below. This last-mentioned function is achieved by means of the internal longitudinal grooves 215,217 that receive the legs 201a,201b,202a,202b of the first and second members 201,202. In this way the sheath 204 is prevented from being rotated in relation to both the first and the second member 201,202 while it still may be longitudinally displaced in relation thereto.

As mentioned above, the intermediary member 203 is provided with a central through-going opening 210 which, in the shown embodiment, has a square cross-section as shown in FIG. 7. The driving rod 205, which extends into the through-going opening 210 in the intermediary member 203, has a similar cross-section that makes it inrotatably but slidably engaged with the intermediary member 203. At the outer end of the linear actuator 205 a gear wheel 221 is provided. When the linear actuator is mounted in a device, such as a medical delivery device, as it will be described below with reference to FIG. 9, the gear wheel 221 is connected to an electric motor that rotates the gear wheel 221 and the driving rod 205. The driving rod 205 has an extension that essentially corresponds to the length of the first member 201 and is retained axially in relation thereto by a not shown manner.

In operation the linear actuator is often initially in its retracted or its expanded state. In the following it is assumed that the linear actuator is initially in its retracted state where the legs 201a,201b,202a,202b of the first and second members 201,202 expand over the entire length of the intermediary member 203. This is possible since each of the legs 201a,201b,202a,202b of the first and second members 201, 202 has a circumferential expanse of less than 90°, while the first and second members 201,202 are rotated 90° in relation to each other. In this initial position the sheath 204 covers the first and the second members 201,202 as well as the intermediary member 203. The pressure plate 209 is positioned just outside the sheath 204. This situation is not shown, but can be easily imagined when viewing FIGS. 7 and 8.

When it is desired to extend the linear actuator, the driving rod 205 is rotated by means of the gear wheel 221. This causes the intermediary member 203 to be rotated and thereby to be displaced telescopically outwards in relation to the first member 201 due to the engagement between the internal threads 206 of the first member 201 and the external threads 211 on the intermediary member 203.

The sheath 204 is also displaced axially in relation to the first member 201 since it follows the intermediary member 203, and due to the engagement between the grooves 215 provided internally in the sheath 204 and the legs 201a,201b of the first member 201, the sheath 204 does not rotate. Since a similar engagement exists between the sheath 204 and the second member 202, i.e. the grooves 217 provided internally in the sheath 204 and the legs 202a,202b of the second member 202, the second member 202 is also prevented from rotating. Therefore, rotation of the intermediary member 203 causes an axial displacement of the second member 202 in relation thereto due to the internal threads 208 provided in the second member 202 and the external threads 212 provided on the intermediary member 203. Since the threads 208,212 are cut in the opposite direction of the threads 206,211, rotation of the intermediary member 203 causes the second member 202 to be displaced out of the sheath 204. The total expansion of the linear actuator is therefore defined as the sum of the displacement of the intermediary member 203 in relation to the first member 201 and the displacement of the second member 202 in relation to the intermediary member 203.

When it is desired to bring the linear actuator back to its initially retracted position, the gear wheel 221 is rotated in the opposite direction which causes the intermediary member 203 and the sheath 204 to be displaced backwards in relation to the first member 201 and the second member 202 to be displaced backwards in relation to the intermediary member 203 and the sheath 204.

The linear actuator according to the embodiment shown in FIGS. 7 and 8 is provided with a scale 222 displayed on one leg 202b of the second member 202. The scale 222 indicates the expansion of the linear actuator or, alternatively, the amount of liquid medicament that has been expelled from a cartridge by means of the linear actuator when it is employed as a piston rod in a medical delivery device.

A linear actuator according to the invention and as shown in the embodiments shown in FIGS. 1–8 may be used in a lot of different devices, such as: a piston rod in a medical delivery device, a lifting jack, or any other appliances provided with a linear actuator. An example of such a use is shown in FIG. 9 in which the linear actuator according to the third embodiment shown in FIGS. 7 and 8 is employed as a piston rod in a medical delivery device 300 for delivering a liquid medicament contained in a container or a cartridge.

The medical delivery device 300 comprises an electric motor 301 that is powered by a battery 302 and it is connected to the gear wheel 221 of the linear actuator via a number of gear wheels 303. The linear actuator is connected to the medical delivery device 300 by means of the end plate 207 in a not shown manner.

The medical delivery device 300 further comprises a cartridge 304 with sidewall that has been partly cut away for better illustration. The cartridge, which may be exchangeable, comprises a cylindrical container provided with a puncturable septum 305 at one end and with a piston or stopper 306 within the container. The piston 306 is shown in a position in which the cartridge 304 has almost been emptied; initially the piston is provided at the opposite end of the cartridge.

In use, a hollow needle is attached to the medical delivery device 300 puncturing the septum 305. The electric motor 301 is then powered to rotate the driving rod 205 by means of the gear wheels 303 and 221. Thereby the linear actuator is expanded as described above and a desired amount of liquid medicament is expelled through the hollow needle. If the cartridge 304 is to be exchanged the linear actuator is retracted by running the electric motor 301 in the opposite direction.

It should be noted that cartridges 304 for liquid medicaments are normally made of a transparent material, such as glass or plastics, which means that the linear actuator is visible through the wall of the cartridge 304. Information provided on the linear actuator is therefore normally visible to the user, and a linear actuator according to the invention is specifically suitable for displaying any such information as described above.

It should also be mentioned that although the sheaths 4,104,204 are provided with closed cylindrical outer surfaces in the embodiments described above with reference to FIGS. 1–8, this need not be the case. The sheaths may be provided with openings in the outer surfaces, if so desired.

We claim:
1. A linear actuator comprising
   a first member provided with threads cut in a first direction;
   a second member provided to be axially displaceable in relation to the first member and being provided with threads cut in a second direction opposite said first direction;
   an intermediary member being engaged with and axially displaceable in relation to the first and second members, respectively, via first and second threads that are complementary to the threads provided on the first and second members, respectively;
   means for preventing rotation of the first member in relation to the second member; and
   drive means for rotationally driving the intermediary member,
wherein
   the threads provided on the first and second members are provided as internal threads;
   the threads provided on the intermediary member are provided as external threads;
   the means for preventing rotation of the first member in relation to the second member comprises a sheath stretching across the intermediary member, said sheath being inrotatably, but longitudinally slidably arranged in relation to the first and second members; and
   the drive means comprises a driving rod that is inrotatably, but longitudinally slidably arranged within the intermediary member.

2. A linear actuator according to claim 1, wherein the sheath is cylinder-shaped with a closed cylinder face.

3. A linear actuator according to claim 1, wherein the first and second members are tube-shaped with smooth exterior surfaces.

4. A linear actuator according to claim 3, wherein the first member has an inner diameter that exceeds an outer diameter of the sheath; that the sheath has an inner diameter that exceeds an outer diameter of the second member; and that the intermediary member generally has a smaller diameter than an inner diameter of the second member except for a part at one end that is provided with the external threads that engage the internal threads of the first member.

5. A linear actuator according to claim 4, wherein the external threads provided on the intermediary member are formed by a plurality of balls protruding from a ball track in a re-circulating ball arrangement.

6. A linear actuator according to claim 4, wherein the first member and the sheath are prevented from being rotated in relation to each other by means of at least one tongue provided in connection with either the first member or the sheath, said tongue engaging a longitudinal groove provided in the other of the two.

7. A linear actuator according to claim 4, wherein the sheath and the second member are prevented from being rotated in relation to each other by means of at least one tongue provided on either the sheath or the second member, said tongue engaging a longitudinal groove provided in the other of the two.

8. A linear actuator according to claim 1, wherein the intermediary member is provided with crossing threads, and that each of the first member and the second member has at least one leg, said legs complementing each other circumferentially around the intermediary member.

9. A linear actuator according to claim 8, wherein each of the first and second members has two legs, each with a circumferential expanse of less than 90°.

10. A linear actuator according to claim 8, wherein the sheath has an inner diameter that exceeds the outer diameters of the first and second members, and that it is provided with internal grooves that engage the legs of the first and second members.

11. A medical delivery device comprising a telescopic piston rod that comprises a linear actuator that comprises
- a first member provided with threads cut in a first direction;
- a second member provided to be axially displaceable in relation to the first member and being provided with threads cut in a second direction opposite said first direction;
- an intermediary member being engaged with and axially displaceable in relation to the first and second members, respectively, via first and second threads that are complementary to the threads provided on the first and second members, respectively;
- means for preventing rotation of the first member in relation to the second member; and
- drive means for rotationally driving the intermediary member, wherein
- the threads provided on the first and second members are provided as internal threads;
- the threads provided on the intermediary member are provided as external threads;
- the means for preventing rotation of the first member in relation to the second member comprises a sheath stretching across the intermediary member, said sheath being inrotatably, but longitudinally slidably arranged in relation to the first and second members; and
- the drive means comprises a driving rod that is inrotatably, but longitudinally slidably arranged within the intermediary member.

12. A medical delivery device according to claim 11, wherein a cartridge with a liquid medicament is provided, and that neither the second member nor the sheath has an outer dimension that exceeds an inner diameter of the cartridge.

13. A medical delivery device according to claim 11, wherein the driving rod is provided with a gear wheel that is connected to a driving mechanism, comprising an electric motor.

* * * * *